United States Patent [19]    [11] Patent Number: 4,755,874
Esrig et al.    [45] Date of Patent: Jul. 5, 1988

[54] EMISSION MICROSCOPY SYSTEM

[75] Inventors: Paul Esrig, Saratoga; Eliezer Rosengaus, Palo Alto; Ezra Van Gelder, Belmont, all of Calif.

[73] Assignee: KLA Instruments Corporation, Santa Clara, Calif.

[21] Appl. No.: 91,682

[22] Filed: Aug. 31, 1987

[51] Int. Cl.$^4$ .............................................. H04N 7/18
[52] U.S. Cl. .................................. 358/106; 358/101; 358/211; 358/225
[58] Field of Search ................. 358/93, 101, 106, 107, 358/211, 225

[56] References Cited

U.S. PATENT DOCUMENTS 4,389,669  6/1983  Epstein ............................... 358/106
4,680,635  7/1987  Khurana ............................. 358/106

Primary Examiner—Howard W. Britton
Attorney, Agent, or Firm—Rosenblum, Parish & Bacigalupi

[57] ABSTRACT

An optical emission microscopy system with a macro optic system having a high numerical aperture for obtaining global views of an integrated circuit Device Under Test (DUT). The DUT is subjected to illumination and stimulation conditions, and images are obtained to form a "global difference" image in which defects, wherever located in the chip, can be discerned by the system operator. The operator can select apparent "defect bright spots" to be further inspected, and zoom in with the higher magnification micro optics system to repeat the image formation steps. "Difference images" are processed to further eliminate noise spots using an improved two-stage filtering operation. The system may be operated under manual or automatic control, and may be interfaced to various data input, storage, and output devices as desired.

27 Claims, 6 Drawing Sheets

X BEFORE SIEVE (EROSION)

IMAGE THRESHOLDED AT A LOW LEVEL
NOISE STILL PRESENT

SIEVE METHOD

BASIC IMAGE ALGEBRA OPERATION : EROSION $A \ominus B = \{p | B_p \subseteq A\}$

X AFTER SIEVE (EROSION)
NOISE ELIMINATED

CONTOUR, TO BE FILLED AFTER SURROUNDING THE SIGHTED PATTERN.

FORMATION OF POINTS CONSTITUTING A PATTERN.

EMISSION MICROSCOPY SYSTEM

BACKGROUND OF THE INVENTION

1. Field of the Invention

The present invention is in the field of emission mioroscopy, and more specifically, integrated circuit inspection systems.

It is well known that in integrated circuit (IC) operation, current conduction through a damaged dielectric can cause it to emit extremely faint light. These photo emissions can be detected by the emission microscope disclosed in U.S. Pat. No. 4,680,635 to Khurana, as follows: The IC or "Device Under Test" (DUT) is placed on the microscope stage with the DUT area to be inspected centered in the axis of the optic system and camera. A light-tight chamber is closed around the microscope, the DUT is illuminated, and, while being viewed through the CRT display by the operator, positioned with the area of interest in the microscope axis. The Z axis elevation of the stage is manually adjusted for better focus if necessary. First, without applying power, the (bright or dark field) illuminated DUT is imaged through the video camera to obtain a "reflected" light top view image of the structural pattern of the DUT. The reflected image is converted into digital form and stored (in memory). Second, the illumination is turned off, and without applying power, any (thermal emissions) background noise light from the inspection area is collected (possibly integrated) and amplified in the analog video camera, and optionally in the digital image computer, to obtain a "background" image, which is digitized and stored. Third, a failure condition "test vector" of voltages (under which a defect in the DUT has previously been detected by an automatic test equipment (ATE) system) is applied by manual switches to the I/O terminals of the (still unilluminated) DUT, causing leakage current conducted through defective dielectric features to emit extremely faint visible and infrared light. This emitted light is collected and amplified to obtain an "emitted" light image, which is digitized and stored. Fourth, the digitized background image is subtracted from the digitized emitted image to provide a "difference" image showing defect emission bright spots, with some noise interference remaining. Fifth, the difference image is filtered or processed by an image processing computer to further separate emitted light points from the random noise bright points inherent to the very large signal amplification done in the primary camera. This processing is conventionally done on the basis of light intensity (gray level) threshold discrimination. However, some noise light emissions are more intense, and produce brighter spots, than the defects of interest, and pass the threshold filter even while the threshold is set high enough to block some interesting defect bright spots. This filtering produces a "processed difference" image. Sixth, the sometimes difficult to recognize "processed difference" image is superimposed over the reflected image of the same area so that photon emission spots can be seen and located with respect to the IC. With this information, a process or failure analysis engineer can, afterwards, refer to the composite layout of the IC, determine the probable cause of failure, and correct the IC design.

Emission microscopy has the advantage that it is a non-destructive technique and does not introduce new defects into the DUT, unlike the conventional technique of stripping layers off of the DUT, which can introduce new defects and is extremely time consuming.

However, this prior art emission microscopy implementation is complicated by the fact that for the defects' extremely faint emissions of light to be detected requires observing the emissions through a lens which maximizes brightness. The amount of light transmitted through a lens is proportional to $NA^2/MAG^2$, where NA is the numerical aperture, and MAG is the magnification, of the lens. This requires a high numerical aperture and low magnification, but there have not previously been commercially available lenses of sufficient quality meeting this requirement. To obtain sufficient brightness with low magnification, the prior art system used a Nikon objective lens with a NA of 0.025, and $1\times$ magnification. Khurana (col. 3 lines 42 through 44) mentions using a lens with NA 0.8 but with a high magnification of $100\times$. When used at a distance practical in a microscope, a lens with this NA limit subtends a field of view only large enough to cover a sub-area, say 1/10, of a typical IC. Thus, the prior art apparatus is only able to examine one sub-area of an IC at a time. Locating defects wherever located in an IC required scanning the entire IC die one sub-area at a time, by successively manually repositioning the stage or optics to line up the camera over each sub-area and repeating the steps of multiple image capture, differencing, and processing for each sub-area, was a cumbersome, error prone, and time consuming process.

Furthermore, it is not uncommon for an IC when stimulated by one test vector to fail due to a defect which only manifests as a consequence of an immediately preceding state during the preceding clock cycle of the IC, when it was stimulated by another test vector. Test vectors cannot be successively set up and applied in real time in the prior art system using manual switches, which generally precludes identifying dynamic failure condition defects.

It is therefore an object of this invention to provide an emission microscopy system which is useable to locate defects in IC's conveniently and quickly.

It is another object to provide a system in which DUT's can be stimulated by application of test vectors in selected sequences and in real time to recreate dynamic failure conditions.

It is another object to provide a process for more precisely locating defects in IC's.

SUMMARY OF THE INVENTION

The present invention achieves these objects by providing an optical emission microscopy system with a combination of visible and near infra-red light detection and image processing techniques. A preferred embodiment of the present invention comprises an optical microscope fitted with a low light level imaging system housed in a light proof enclosure. Under the microscope, a stage holding the device under test (DUT) is capable of moving in X, Y, and Z directions. In a typical application, a packaged IC device with the top removed is placed in a socket through which I/O pins are connected to voltage potentials controlled by the computer. Steady state DC power is used in most inspections, although selectable logic levels may be applied to any I/O pin. It is also possible to interface the DUT to an ATE system. The test vector (or sequence of test vectors) is applied to recreate the exact condition under which the device is already known to have failed. Three magnification powers are available: $1\times$ in the macrostation, and 10× and 40×, or optionally 100×, in the microstation. The low light level imaging system comprises a microchannel plate image intensifier, which is coupled to a very sensitive solid state camera capable of integrating photons over selectable periods of time.

Emission microscopy according to the present invention locates silicon oxide dielectric and passivation layer defects of the following types: process or structure induced failures such as oxide rupture at corners; junction breakdowns; electrostatic discharge (ESD) damage usually associated with I/O pin leakage; latch-up conditions; saturated transistors; hot electron (impact ionization) effects that occur dynamically in switching transistors; and electromigration voiding or "patch emission" at high currents.

DETAILED DESCRIPTION OF THE INVENTION

Figure 1:
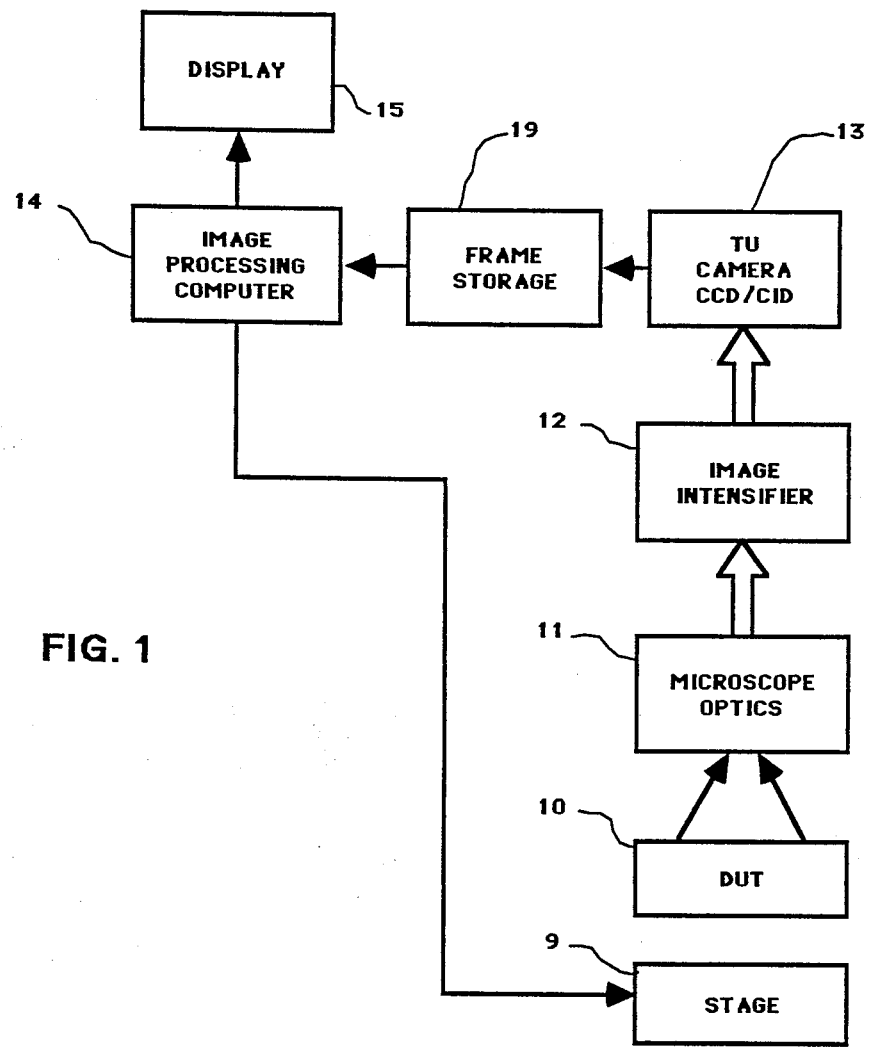
FIG. 1 is a schematic block diagram illustrating a preferred embodiment of the emission microscopy system of the present invention.
Figure 2:
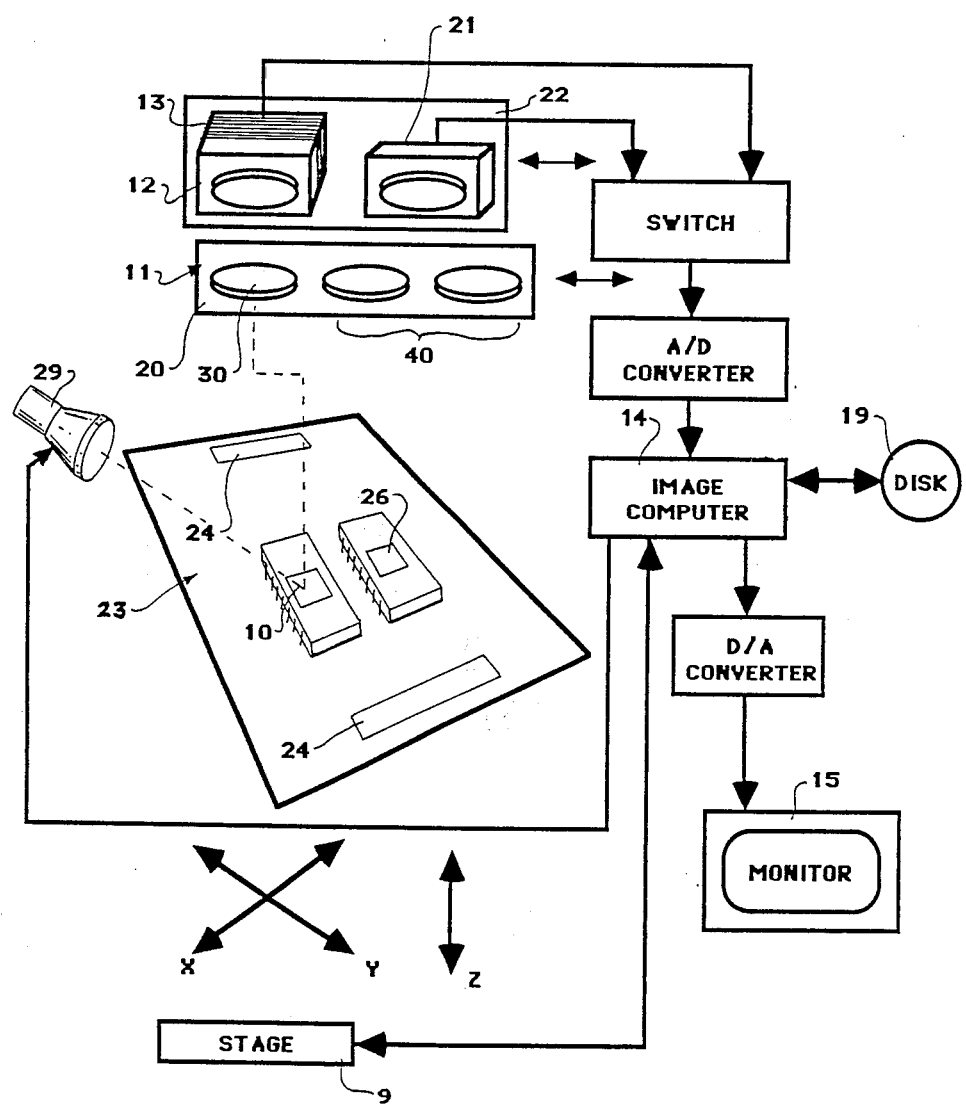
FIG. 2 is a diagram showing how the present invention arranges the macro and micro optic system relative to the image acquisition and auxiliary cameras of the present invention.
Figure 3:
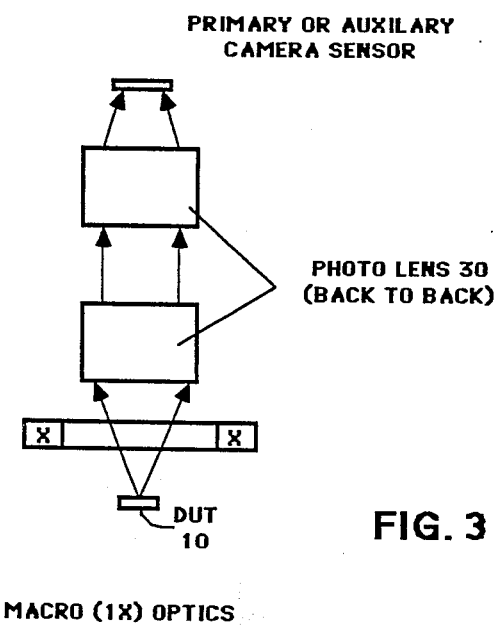
FIG. 3 shows one possible arrangement of conventional camera lenses to form a high numerical aperture lens.
Figure 11:
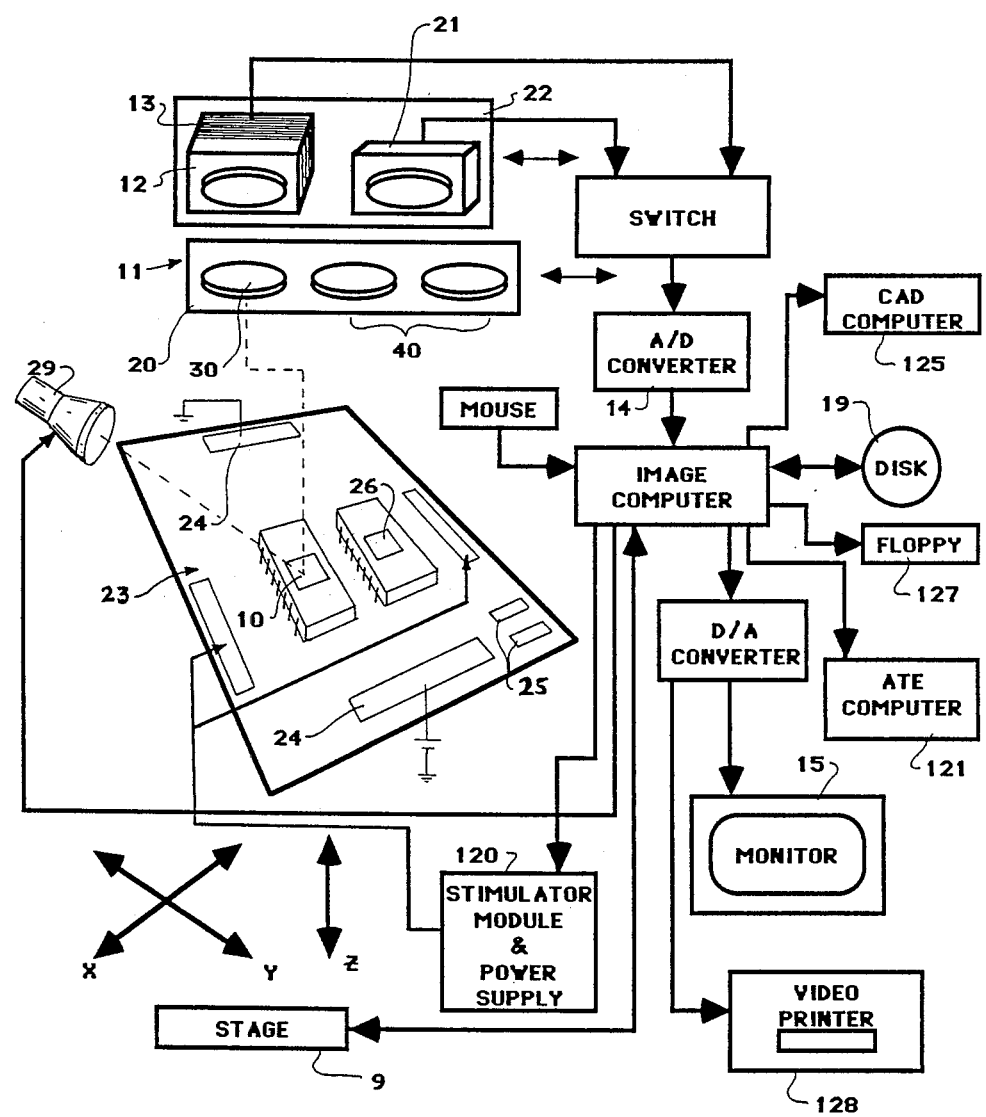
FIG. 11 shows additional features in the preferred embodiment of the present invention.

Referring to FIGS. 1 and 2, a preferred embodiment of the present invention is illustrated and comprises stage means 9 for mounting a device under test 10 to be inspected, optical means 11, light intensifier means 12, and primary video camera or other solid state optical-to-electronic analog converter means 13 with analog integration (time-exposure) capability, video image signal processing (computer) means 14, and display means 15. As shown in FIG. 2, optical means 11 includes at least one micro-optical system 40 comparable to the prior art system, and further includes macro optic system 30 having a high numerical aperture of at least 0.025 and preferably in the range from 0.17 to 0.34 or higher. The micro and macro optics are both held by a moveable slide 20 which is preferably moved by a stepper motor actuator, not shown, under control of computer 14. Also arranged above optic means 11, and beside primary camera means 13, is an auxiliary camera 21 for providing supplementary views to the system operator. Primary camera 13 and auxiliary camera 21 are both held by moveable bracket means 22 which is also preferably moved automatically by an actuator under the control of computer 14. Optical means 11 and both camera means 13 and 21 are movable with respect to stage 9, either by movement of the optical and camera systems or by movement of the stage, in either case preferably automatically under control of computer 14. As shown in FIG. 2, stage 9 supports a socket adaptor module 23 having a zero insertion force (ZIF) socket which holds the DUT 10. Socket adaptor module 23 has banks 24 of appropriate numbers of local 3-way switches for connecting respective I/O pins of the DUT 10 to either a supply voltage, a ground voltage, or a high impedance (open circuit) Z state. Module 23 preferably has two additional input BNC connector terminals 25 for applying additional signals such as a clock signal to selected individual I/O pins of DUT 10. Module 23 is preferably also provided with a second socket 26 for mounting a second DUT for comparisons with DUT 10. As shown in FIG. 11, the preferred embodiment also includes a stimulator module 120 (optionally available from KLA Instruments Corporation) capable of receiving and applying multiple test vectors to DUT 10 or storing on disk 19 a 4000 to 5000 test vector sequence set up. Stimulator module 120 may be programmably controlled by computer 14 to apply test vectors in selected sequences and to stop on, and hold, a selected vector. Further, stimulator module 120 may be connected through computer 14 to a serial interface (either RS-232 or Ethernet) for receiving test vectors from an ATE system 121.

Referring to FIGS. 1 and 2, primary camera 13 works with light intensifier 12 which is preferably a dual microchannel plate intensifier, which is gated to control timing of exposures, and which has an amplification or gain factor of 50 to 60 thousand.

The emission microscopy system user, not shown, begins an inspection operation by inserting a DUT 10 into the module 23 socket. Optic system support bracket 20 is positioned as necessary to center macro optics 30 in the axis of primary camera 13. The door is closed and DUT illumination means 29 is turned on. In the preferred embodiment using a one power magnification macro optics station, an operator can, in one view, inspect a one centimeter by one centimeter die area. While viewing DUT 10 via display 15, the operator moves module 23 so that the entire DUT die is visible in the field of view of macro optics 30 and primary camera 13. The camera axis coincides with a DUT point designated for the reference origin for coordinates of defects to be found. For better focus, the opertor can also adjust the Z stage. Using either manual switches 24 or, with switches 24 in the neutral position, using automatic stimulator module 120, module 23 is set up to apply a test vector (or sequence of test vectors) to the I/O pins of the DUT. Reflected, background, and emitted images are formed as explained above.

The intensified image enters primary camera 13. Camera 13 may be a charge coupled device (CCD), a charge injection device (CID), or other suitable type of optical to electronic analog converter, with the capability to perform analog integration. The image is preferably integrated in the analog intensifier until the average pixel value throughout the field of view reaches a gray level value midway in the available range of gray levels, say until reaching a level of 128 out of 256 gray levels available, to leave an adequate range for integrating values of actual "bright points". Analog integration without truncation errors is preferable over digital integration by computer 14. The amplified background image is substracted from the amplified emitted image to give the difference image as explained above. Then, after processing, the difference image is superimposed upon the previously stored reflected image to give a macro or "global" composed image in which defects wherever located in the chip can be discerned by the system operator. This global view eliminates the prior art necessity of repositioning the micro optics system and repeating the image capture, differencing and overlay steps for each sub-area potentially having a defect in the DUT. With this macro or global view, the operator can select possible defect bright spots in local area windows to zoom in on for closer inspection with the higher magnification micro optics system 40.

The operator, or optionally the computer automatically, moves the long working distance (LWD) micro lens 40 into the axis of primary camera 13, and adjusts the position of stage 9 relative to the axis of camera 13 on one of the apparent defect bright spots to be further inspected. The test vector voltages are removed, and the chamber interior is illuminated as before to repeat the imaging process. For each suspected defect bright spot to be inspected, the micro optics system 40 is used to form another set of reflected, background, emitted and difference images. Each micro difference image is then processed to further eliminate remaining noise, using, according to the present invention, an improved two-stage filtering operation.

Figure 4:
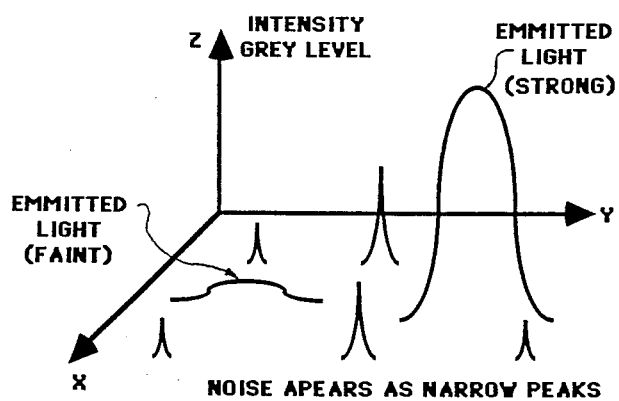
FIG. 4 is a three dimensional plot of a difference image showing light emitted from areas in an IC in the XY plane, and showing light intensity in the Z direction.
Figure 5:
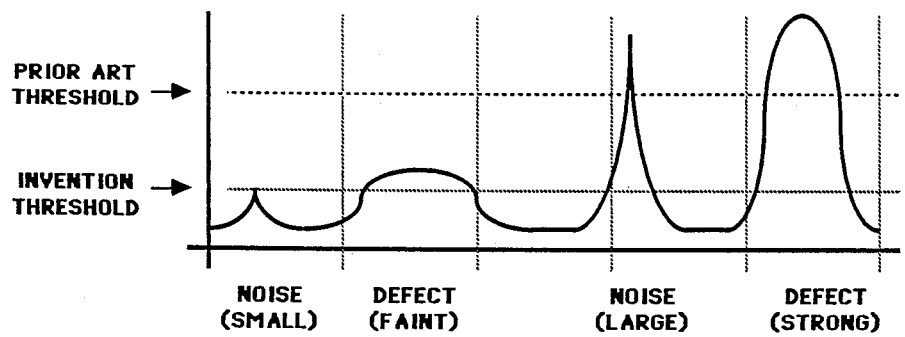
FIG. 5 shows how noise signals not filtered out by the prior art technique can be filtered out by the present invention technique.
Figure 6:
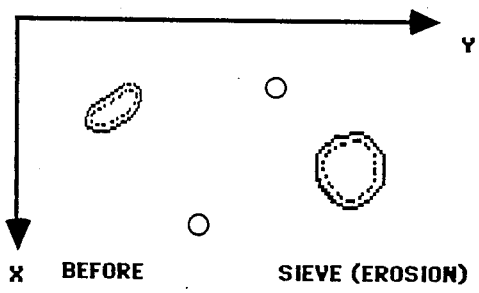
FIG. 6 is a plot of the difference image after threshold filtering with some noise still present.
Figure 7:
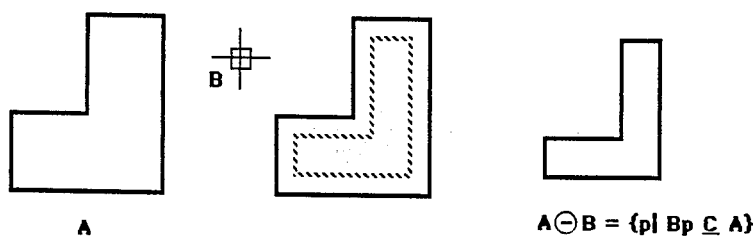
FIG. 7 illustrates the image processing second filtering step of erosion.
Figure 8:
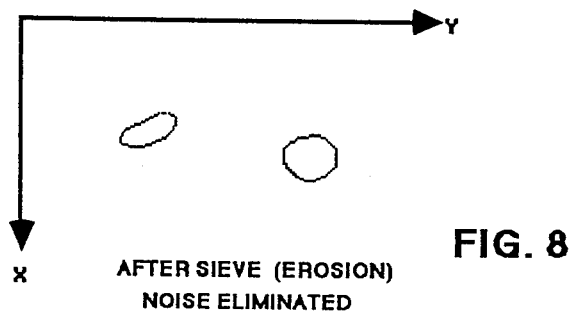
FIG. 8 shows the processed image after erosion to eliminate noise.

Referring to FIG. 4, a sub-area of IC 10 is plotted in the XY plane with sub-area noise and defect bright spot intensities plotted on a gray level scale along the Z axis. If this micro difference image is filtered according to the prior art technique of threshholding as shown in FIG. 5, intense noise spots will pass while weak bright spots are blocked. However, the inventors of the present invention have realized that the interesting defect bright spots, whatever their intensity, characteristically extend over a certain minimum area or have other spacial characteristics, and that this characteristic may be used for a second processing step of improved filtering. Second stage processing is based on the image algebra operation of "erosion" as illustrated in FIG. 7 in which the input image A is depicted as a solid line while the transformed image is shown by a dashed line. This allows the first stage threshhold to be lowered to pass weak defect bright spots, while intense but small area noise spots are removed. The erosion or sieve processing removes noise from the FIG. 6 image to produce an image without noise as shown in FIG. 8.

The above explained technique of erosion is not the only technique of removing random noise points which may be used. For example, it is also possible to do bright spot sizing by "morphological operations" or "low pass filtering" as explained in *Digital Image Processing* by W. K. Pratt, Published by J. Wiley, N.Y. (1978). It is also possible to do the high level machine vision technique of "connectivity analysis" as explained in *Computer, Vision* by D. Ballard & C. M. Brown, published by Prentice-Hall, Englewood Cliffs N.J. (1982). Other techniques are explained in *Algorithms for Graphics and Image Processing* by Theo Pavidis, published by the Computer Science Press, Rockville MD. (1982).

Figure 9:
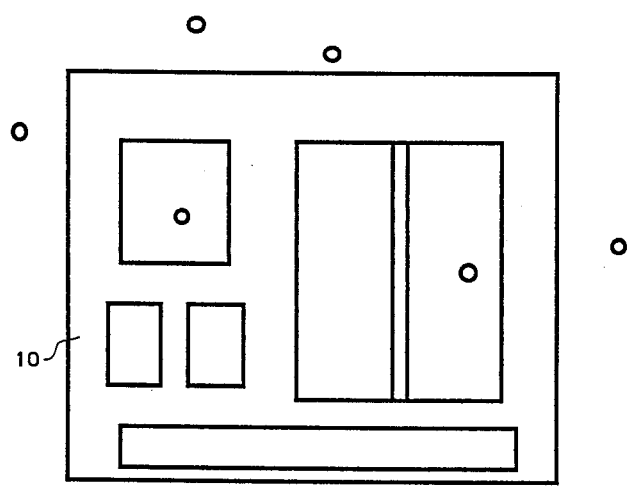
FIG. 9 shows how the present invention applies context discrimination.
Figure 10:
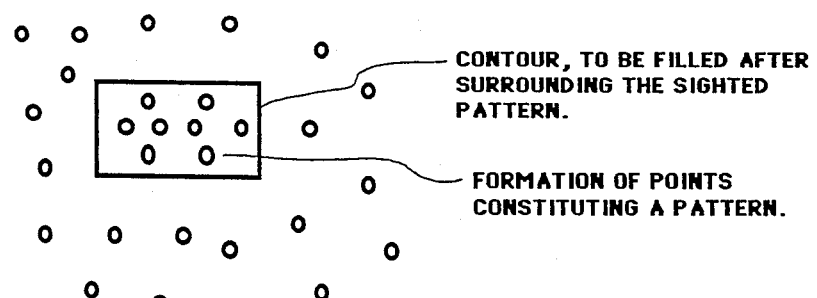
FIG. 10 illustrates the paint operation possible with the present invention.

According to the present invention, micro difference image processing may also use context discrimination by superimposing the micro difference image onto a copy of the reflected image, as shown in FIG. 9. This allows areas of the die which are not suspected of having defects, or which are outside the circuit altogether, to be identified and eliminated from suspicion of having defects.

The present invention also provides a "paint" capability which allows a system operator who recognizes a defect bright spot pattern to circumscribe it with a rectangle, elipse, circle, or other contour, and then fill or "paint" in the contour around the defect, and thereby force the computer 14 to treat the painted area as having passed the first and second stage filters and been recognized normally (by the system). Use of the paint feature is automatically noted as "retouched" by computer 14 on the processed micro difference image output by the system, so that the painted-in patterns will not later be mistaken for normally identified patterns.

The difference image processing algorithm (preferably as shown in the Flow Chart of FIG. 13) operates with adjustable parameters for noise and defect bright spot gray level sensitivities and confidence margins.

Figure 13:
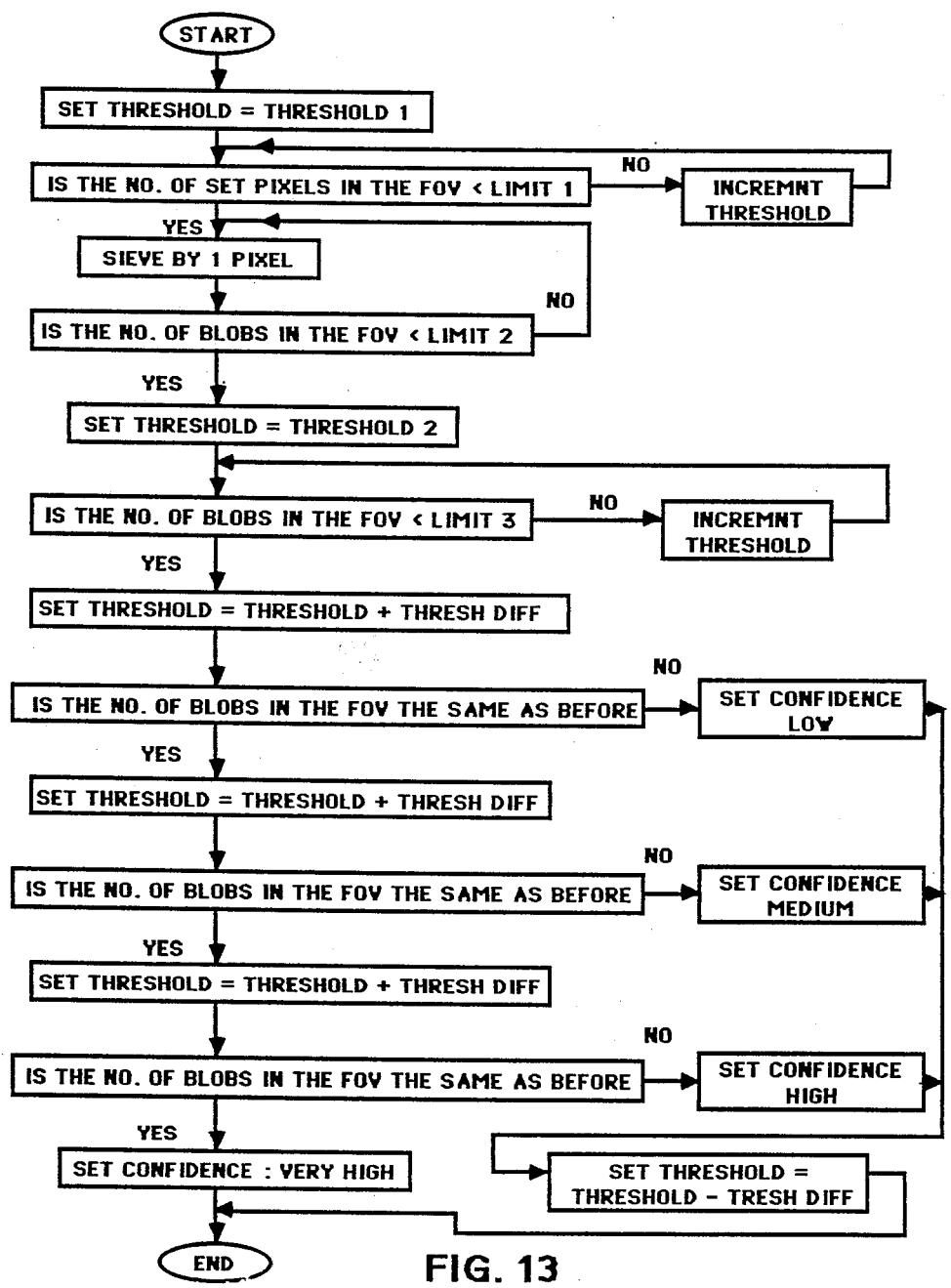
FIG. 13 is a flowchart of the algorithm preferably used for automated noise elimination.

In the preferred embodiment, after the macro difference image is obtained and apparent defects are approximately located, computer 14 can automatically replace the macro optic system 30 with the micro optic system 40, move stage 9 so that the first one of the recognized bright spots is in the axis of the micro optic system 30 and camera 13, and execute the image formation, differencing, and processing steps, with selectable confidence levels, according to the FIG. 13 algorithm.

Each "processed micro difference image" is superimposed onto the reflected image of the same area. However, because the reflected image was received through noise-amplifying intensifier 12 and primary camera 13 and converted into digital form for storage, the retrieved reflected image may be of unsatisfactory quality for the operator to use in correlating defect locations to coordinates of the IC. Therefore, in addition to the primary camera system 13, the present invention also provides an auxillary camera system 21 as shown in FIG. 2. The prior art design did not appreciate that the primary camera 13 has inadequate resolution for small features, and merges groups of features if they are small in size. The auxillary camera is an ordinary high resolution video camera, without an image intensifier, which provides higher quality images, comparable to microscope eye piece images, side-by-side with the processed image on display 15, for the operator to better distinguish features.

Besides comparisons with a stored reflected image, the processed micro difference image may also be compared against a reflected image of a corresponding second device under test 26, FIG. 2. In addition, the processed difference image may be compared against a stored image of another IC of the same type known to be free of defects. Alternately, image computer 14 may be provided with an interface to a computer aided design (CAD) system 125, FIG. 11, through which the emission microscopy system under manual or automatic control can retrieve the composite layout image of each area of the IC. This facilitates identification of defect types and locations to within ±1 micron in the preferred embodiment.

The invention also preferably includes means for the processed difference and superimposed macro and micro images of each area to be output to alternate display devices including a hard disk 126, a floppy disk 127, or a video image printer 128, FIG. 11.

The interior chamber illumination level is also preferably automatically controlled by computer 14 to produce good images regardless of variations in reflectivity of various DUTs.

The preferred embodiment is operated with commands input conveniently by a "mouse and-menu" operator interface system.

Figure 12:
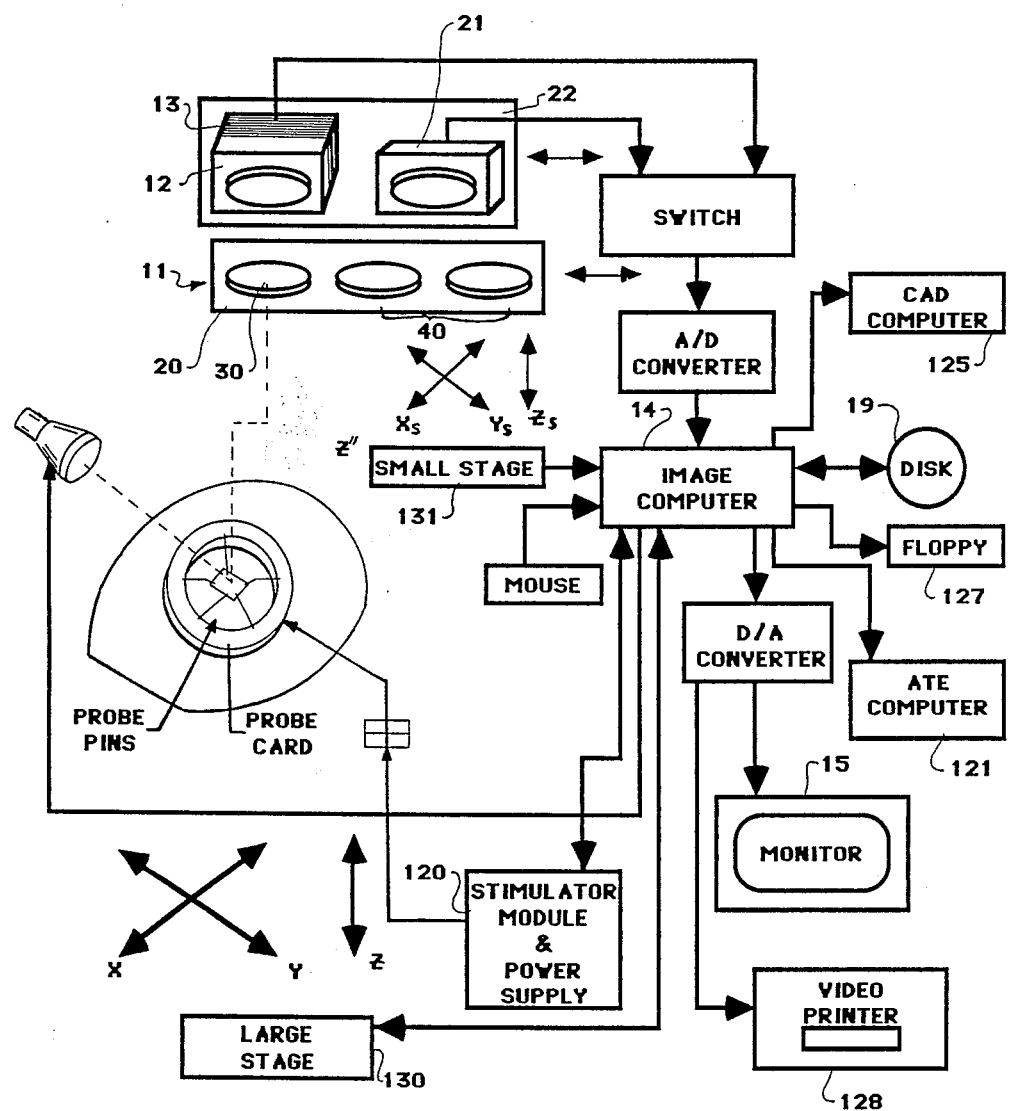
FIG. 12 shows a second embodiment of the invention capable of inspecting dies in a larger wafer before separation.

For inspection of IC dies unseparated in a semiconductor wafer, a large stage 130 supporting a small stage 131, both stages being automatically moveable in X, Y and Z directions under control of computer 14, is shown in FIG. 12.

This system provides process and reliability engineers with evidence of process and/or structure induced oxide failures as well as several other types of dialectrically failures and thereby helps increase device yield and reliability.

We claim:

1. Emission microscopy means for detecting light emitted from defects in dielectric layers of integrated circuit devices in response to test vector signals applied to the input and output terminals of the integrated circuit device, comprising:
   mounting means for holding the device under test to be inspected;
   optical means including macro optic means having a high numerical aperture for obtaining global optical images of said device under test and including micro optic means for alternatively obtaining micro optical images of sub-areas of said device under test;
   primary camera means for converting said optical images into analog electronic signals, said camera means including light intensifier means and being capable of integrating the analog electronic signals;
   video image signal processing means for processing said analog electronic signals; and
   video image display means for displaying signals processed by said video image processing means.

2. Apparatus as in claim 1 wherein said macro optic means has a numerical aperture of at least 0.025.

3. Apparatus as in claim 2 further including illumination means for illuminating said device under test at light intensity levels automatically controlled by said computer means.

4. Apparatus as in claim 2 wherein operations of said system are controlled by said image processing means under the control of mouse input means.

5. Apparatus as in claim 2 wherein said display means includes storage means.

6. Apparatus as in claim 5 wherein said storage means includes means of providing a previously verified good integrated circuit image by said display means and comparison with said displayed processed difference image.

7. Apparatus as in claim 5 wherein said storage means includes floppy disk storage means.

8. Apparatus as in claim 5 wherein said storage means includes video image printer means.

9. Apparatus as in claim 2 wherein said mounting means and said optical means are moveable with respect to each other automatically under programmed control by said signal processing means.

10. Apparatus as in claim 9 wherein said mounting means includes wafer chuck means, probe means, and wherein both said mounting means and said optical means are moveable with respect to each other automatically under programmed control by said signal processing means.

11. Apparatus as in claim 9 wherein said mounting means includes a socket adaptor module with local switches and auxillary signal input means for applying selected test vector voltages to said input and output terminals.

12. Apparatus as in claim 11 wherein said mounting means includes means to mount a second device under test adjacent the first mentioned device under test, and said module includes means for applying test vectors to said second device under test.

13. Apparatus as in claim 9 further including auxillary camera means for providing a display image to supplement the image provided by said primary camera means.

14. Apparatus as in claim 9 wherein said micro optic means includes a plurality of lenses means having magnification powers in the range between 10 and 100 times, and is engageable in the optical axis of said primary camera by the computer.

15. Apparatus as in claim 9 wherein said mounting means includes stimulator module means for programmably applying selected test vectors to I/O terminals of a device under test inserted into said socket adaptor module.

16. Apparatus as in claim 15 further including CAD interface means for said image signal processing means to access IC composite layout images from a computer aided design system.

17. Apparatus as in claim 15 including ATE interface means for connecting said stimulator module to receive test vectors provided from an automatic test equipment system.

18. Apparatus as in claim 17 wherein said stimulator module is programmable to apply selected test vectors in a selected order through said stimulator module to a device under test.

19. A method of detecting light emitted from defects in dielectrics located at unknown coordinates in an integrated circuit device comprising the steps of:
   obtaining a reference image of said device;
   forming a background image of collectable noise;
   applying electrical voltages to selected terminals of the integrated circuit device so as to cause light to be emitted at the locations of defects contained therein;
   forming an emitted light image of said integrated circuit including the light emitted from defects contained therein;
   forming a difference light image of said integrated circuit by subtracting said background image from said emitted image;
   processing said difference image to remove noise and to produce a processed macro difference image;
   superimposing said processed macro difference image onto said reflected image to form a superimposed image;
   identifying defect bright spots on said superimposed image;
   compiling a list of coordinates of said bright spots;
   replacing said macro lens with a micro lens;
   moving the axis of said micro lens over a first set of coordinates from said list;

forming a difference image of the local area in a window around said set of coordinates;

processing said difference image to remove noise and to produce a processed micro difference image;

superimposing said processed difference image over said micro reflected image; and comparing said superimposed image to a reference image of said integrated circuit to locate coordinates of said defect, more precisely relative to said integrated circuit.

20. A method as in claim 19 wherein said step of obtaining a reference image includes illuminating said integrated circuit; and forming a reflected light image of said illuminated integrated circuit.

21. A method as in claim 19 wherein said step of processing includes filtering said image by spatial characteristics discrimination such as "erosion".

22. A method as in claim 19 wherein said step of processing includes performing context discrimination on said difference image.

23. A method as in claim 19 wherein said step of processing includes the step of painting said difference image.

24. A method as in claim 23 including the step of annotating said difference image.

25. A method as in claim 19 wherein said step of processing is programmably automatically performed.

26. A method as in claim 25 wherein said processing can be done with selectable gray level sensitivity.

27. A method as in claim 26 wherein said processing is done with selectable confidence levels.

* * * * *